United States Patent
Maly (10) Patent No.: US 10,660,673 B2
(45) Date of Patent: May 26, 2020

(54) BONE IMPLANT HAVING TETHER BAND

(71) Applicant: Richard S. Maly, San Diego, CA (US)

(72) Inventor: Richard S. Maly, San Diego, CA (US)

( * ) Notice: Subject to any disclaimer, the term of this patent is extended or adjusted under 35 U.S.C. 154(b) by 0 days.

(21) Appl. No.: 15/533,239

(22) PCT Filed: Dec. 3, 2015

(86) PCT No.: PCT/US2015/063818
§ 371 (c)(1),
(2) Date: Jun. 5, 2017

(87) PCT Pub. No.: WO2016/090180
PCT Pub. Date: Jun. 9, 2016

(65) Prior Publication Data
US 2017/0360483 A1    Dec. 21, 2017

Related U.S. Application Data (60) Provisional application No. 62/086,943, filed on Dec. 3, 2014.

(51) Int. Cl.
*A61B 17/064* (2006.01)
*A61B 17/70* (2006.01)
*A61B 17/86* (2006.01)

(52) U.S. Cl.
CPC ...... *A61B 17/7053* (2013.01); *A61B 17/0642* (2013.01); *A61B 17/863* (2013.01); *A61B 17/8605* (2013.01); *A61B 17/8685* (2013.01); *A61B 17/8695* (2013.01); *A61B 17/7082* (2013.01); *A61B 2017/0641* (2013.01)

(58) Field of Classification Search
CPC ............................................ A61B 2017/0641

USPC .................................................. 606/246–331
See application file for complete search history.

(56) References Cited

U.S. PATENT DOCUMENTS

| | | | |
|---|---|---|---|
| 4,834,752 A | 5/1989 | Van Kampen | |
| 4,988,351 A | 1/1991 | Paulos et al. | |
| 5,314,427 A * | 5/1994 | Goble | A61B 17/0642 411/457 |
| 5,601,558 A | 2/1997 | Torrie et al. | |
| 5,690,629 A * | 11/1997 | Asher | A61B 17/7044 606/265 |
| 5,720,765 A | 2/1998 | Thal | |

(Continued)

FOREIGN PATENT DOCUMENTS

| | | |
|---|---|---|
| CN | 1953714 | 4/2007 |
| CN | 101146486 | 3/2008 |

(Continued)

OTHER PUBLICATIONS

European Patent Office, European Search Reportfor Appln. No. 15866071.2, dated Jun. 8, 2018, 9 pgs.

(Continued)

*Primary Examiner* — Pedro Philogene
(74) *Attorney, Agent, or Firm* — John V. Daniluck; Dentons Bingham Greenebaum LLP (57) ABSTRACT

Devices and methods useful in surgical processes that require structural attachment to bone such as spinal vertebrae. More specifically, an improved bone implant having a band there through for the purpose of correcting and/or preventing curvature of the spine.

11 Claims, 6 Drawing Sheets

(56) References Cited

U.S. PATENT DOCUMENTS

| | | | |
|---|---|---|---|
| 5,947,969 A * | 9/1999 | Errico | A61B 17/7044 606/308 |
| 6,296,643 B1 | 10/2001 | Hopf et al. | |
| 6,299,613 B1 * | 10/2001 | Ogilvie | A61B 17/0642 606/279 |
| 6,575,987 B2 | 6/2003 | Gellman et al. | |
| 7,585,311 B2 | 9/2009 | Green et al. | |
| 8,366,748 B2 | 2/2013 | Kleiner | |
| 8,529,609 B2 * | 9/2013 | Helgerson | A61B 17/7064 606/247 |
| 8,894,685 B2 * | 11/2014 | Mickiewicz | A61B 17/7064 606/247 |
| 8,992,579 B1 | 3/2015 | Gustine et al. | |
| 9,119,678 B2 | 9/2015 | Duggal et al. | |
| 2001/0031966 A1 | 10/2001 | Tormala et al. | |
| 2003/0105465 A1 | 6/2003 | Schmieding et al. | |
| 2004/0111088 A1 | 6/2004 | Picetti | |
| 2007/0212190 A1 | 9/2007 | Monday et al. | |
| 2008/0234758 A1 | 9/2008 | Fisher et al. | |
| 2010/0106195 A1 * | 4/2010 | Serhan | A61B 17/0642 606/279 |
| 2013/0110183 A1 * | 5/2013 | Duggal | A61B 17/7064 606/328 |
| 2013/0338715 A1 * | 12/2013 | Daly | A61B 17/7032 606/263 |
| 2014/0066991 A1 | 3/2014 | Marik | |

FOREIGN PATENT DOCUMENTS

| | | |
|---|---|---|
| CN | 104306057 | 1/2015 |
| JP | 2001518813 | 10/2001 |
| JP | 2004535217 | 11/2004 |
| JP | 2008534050 | 8/2008 |
| JP | 201359674 | 4/2013 |
| WO | 2016122208 A1 | 8/2016 |

OTHER PUBLICATIONS

IP AU, Serial No. 2015358390, Examination Report No. 1, 3 pgs dated Aug. 23, 2019.
EP 15 866 071.2, Response to EP Search Report, 11 pgs dated Dec. 28, 2018.
EP 15 866 071.2, EPO Office Action, 6 pgs dated Aug. 2, 2019.
SIPO, CN 201580075283.9, First Office Action, 9 pgs dated Jul. 29, 2019.
JPO, JP2017-530215, Office Action, 9 pgs dated Sep. 19, 2019.

* cited by examiner

(Prior Art)

BONE IMPLANT HAVING TETHER BAND

RELATED APPLICATIONS

This application is a United States National Stage Application claiming priority under 35 U.S.C. 371 from International Patent Application No. PCT/US15/63818 filed on Dec. 3, 2015, which claims the benefit of priority from U.S. Provisional Application No. 62/086,943, filed on Dec. 3, 2014, the entire contents of which are herein incorporated by reference.

FIELD OF THE INVENTION

The present invention pertains generally to devices and methods useful in surgical processes that require structural attachment to bone such as spinal vertebrae. More specifically, the present invention is particularly, but not exclusively useful, as an improved bone implant having a band there through for the purpose of correcting and/or preventing curvature of the spine.

BACKGROUND OF THE INVENTION

Spinal fusion have been known as a procedure providing stabilization of the spine for sufferers of ailments such as scoliosis, or other pathologic curvatures of the spine. Initially in performing this procedure, supplemental bone is laid down and plates and/or screws, which are configured to receive a rod, are inserted into the vertebrae of the spine so that the spine is stabilized and/or fixed from thither curvature by means of arresting further spinal growth. The plates are specifically configured to specially designed pedicles that protrude from a posterior part of the spine. Spinal fusion, used to treat scoliosis and other pathologies of the spine, is utilized in mature patients wherein the spine is fully grown. However, it is not particularly well suited for juvenile patients wherein the spine is still growing.

Adolescent idiopathic scoliosis is the prevalent form of scoliosis and typically occurs after the age of 10. Girls are more likely to develop this form of scoliosis which may have a genetic component as the cause. Although minor curvature of the spine may be caused by injury or infection, structural scoliosis of unknown origin, may result from any of a number of causes leading to its development. A healthy spine has a subtle S shape starting from the cervical spine down to the lumbar spine when viewed from the side and a largely straight line along the y-axis when viewed from front or back. Deviations of the spine from the y-axis, known as lateral curvature, are categorized as thoracic, lumbar, thoracolumbar and double. A minor curvature, defined as a deviation of the spine of 10% or less from the y-axis may be treated noninvasively through observation or bracing. Significant curvature, defined as greater than 10% deviation from the y-axis is largely treated surgically. Since scoliosis is a progressive condition, if left untreated may be debilitating effects on the entire body, including but not limited to, rib deformity, shortness of breath, digestive problems, chronic fatigue, acute or dull back pain, leg, hip, and knee pain, acute headaches, mood swings, and menstrual disturbances.

In light of the above, doctors have recently begun employing techniques on younger patients wherein patients must lie on their sides and plates and/or screws are attached to a lateral side body of the vertebrae. This procedure is however complicated and the lungs and other vital tissues being in the way while performing the task of inserting a plate and/or screws to a side, anterior or lateral portion of the spine. Specifically, the lung must often be collapsed and a sleeve inserted into the region allowing the surgeon to work through. However once completed, the side having the implant will have its growth halted in order to allow the opposite side to grow and "catch up" to the other side thereby straightening the curvature. Further complicating matters, the plates and/or screws configured to receive the rods have features and/or components that protrude and may aggravate lung and/or other adjacent tissues. One difference between the procedure of the present invention and the prior spinal fusion procedure, the metal rod of the prior art procedure is replaced by a cord, wherein the cord is more readily adjustable and is lower profile. Therefore, it is an object of the present invention to provide an improved device and cord/band capable of comfortably performing the function of attaching to a vertebrae, on the side thereof, or to other bony structures or anatomy.

SUMMARY OF THE INVENTION

The present invention is an improved spine implant for the treatment of curvature of the spine.

It is an object of the present invention to provide a bone implant for treatment of curvature of the spine that is compatible with a growing spine in an adolescent or juvenile patient.

It is another object of the present invention to provide a bone implant comprised of a staple, bone screw and looking screw.

It is yet another object of the present invention to provide a hone implant wherein, the staple has a domed upper surface and a domed lower surface and rounded edges in order to reduce the irritation of soft tissue surrounding the spine.

It is still another object of the present invention to provide a bone implant wherein the staple is further comprised of a plurality of spike protruding from the domed lower surface such that the spikes facilitate stable fixation to the vertebral bone and also the dispersion of forces exerted on the vertebral hone to which it is attached.

It is another object of the present invention to provide a hone implant wherein the bone screw is comprised of a first tapered end and a second flat end, the first tapered end and the second flat end defining the body of the length of the bone screw.

It is still another object of the present invention to provide a bone implant wherein the bone screw has threads along the outer circumference of the length of said bone screw, the threads being of varying patterns or pitches.

It is a further object of the present invention to provide a bone implant wherein the staple has at least an inner, lower set of threads corresponding with at least one set of threads on the hone screw such that the staple and bone screw lock together upon insertion to the vertebral bone.

It is yet another object of the present invention to provide a bone implant wherein the staple has an inner flat surface wherein the second flat end of the bone screw lies flush with and adjacent to the inner flat surface.

It is another object of the present invention to provide a bone implant wherein the locking screw is comprised of a domed upper surface and a domed, or otherwise configured, lower surface and further having threads around the outer circumference of the locking screw the threads being disposed between the domed upper surface and the domed lower surface.

It is a further object of the present invention to provide a bone implant wherein the staple has an inner set of threads, the inner threads corresponding to the threads on the outer circumference of the locking screw.

It is yet another object of the present invention to provide a bone implant wherein the installed implant creates a smooth margin with the vertebral bone to which it is attached.

It is another object of the present invention to provide a method of installing the bone implant for treatment of a curvature of the spine.

A first embodiment of the present invention provides a bone implant for treatment of curvature of the spine that is compatible with a growing spine in an adolescent or juvenile patient.

A second embodiment of the present invention provides a bone implant comprised of a staple, bone screw and locking screw.

A third embodiment of the present invention provides a bone implant wherein the staple has a domed upper surface and a domed lower surface in order to reduce the irritation of soft tissue surrounding the spine.

A fourth embodiment of the present invention provides a bone implant wherein the staple is further comprised of a plurality of spike protruding from the domed lower surface such that the spikes facilitate secure fixation as well as the dispersion of forces exerted on the vertebral bone to which it is attached.

A fifth embodiment of the present invention provides a bone implant wherein the bone screw is comprised of a first tapered end and a second flat end, the first tapered end and the second flat end defining the body of the length of the bone screw.

A sixth embodiment of the present invention provides a bone implant wherein the bone screw has threads along the outer circumference of the length of said bone screw, the threads being of varying patterns or pitches.

A seventh embodiment of the preset invention provides a bone implant wherein the staple has at least an inner, lower set of threads corresponding with at least one set of threads on the bone screw such that the staple and bone screw lock together upon insertion within the vertebral bone.

An eighth embodiment of the present invention provides a bone implant wherein the staple has an inner flat surface wherein the second flat end of the bone screw lies flush with and adjacent to the inner flat surface. In an alternative embodiment, the bone screw is available to slightly engage the locking screw.

A ninth embodiment of the present invention provides a bone implant wherein the locking screw is comprised of a domed upper surface and a domed lower surface and further having threads around the outer circumference of the locking screw the threads being disposed between the domed upper surface and the domed lower surface.

A tenth embodiment of the present invention provides a bone implant wherein the staple and the bone screw each possess a corresponding cut out, the cut out accommodating the placement of a tether cord.

An eleventh embodiment of the present invention provides a bone implant wherein the installed implant creates a smooth margin with the vertebral bone to which it is attached.

A twelfth embodiment of the present invention provides a bone implant wherein the staple and bone screw are combined in a single unit, wherein the single unit possesses the feature of the top surface of the staple and the lower features of the bone screw.

A thirteenth embodiment of the present invention provides a method of installing the bone implant for treatment of a curvature of the spine, the method comprising:

attaching a staple to a vertebrae of the spine of a patient;
inserting a bone screw through the staple and into the vertebrae;
tightening the bone screw using a screwdriver tool;
aligning a tether cord perpendicular to the vertebrae and along a cut-out in the top of the staple;
inserting the locking screw into an exposed flat end of the bone screw; and
tightening the locking screw using a screwdriver tool;
wherein the tightening of the locking screw secures the bone implant into the vertebrae to which it is attached.

The invention can be better visualized by turning now to the following drawings wherein like elements are represented by like characters.

BRIEF DESCRIPTION OF DRAWINGS

The novel features of this invention, as well as the invention itself, both as to its structure and its function, will be best understood from the accompanying drawings, taken in conjunction with the accompanying description, in which similar reference characters refer to similar parts, and in which:

FIG. 3 illustrates an additional side view thereof showing a screw configured to receive a cord there through;

DETAILED DESCRIPTION OF THE INVENTION

Figure 1:
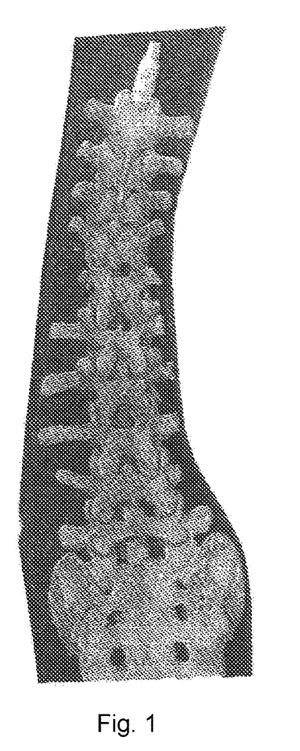
FIG. 1 illustrates a rear view of a spine having an exemplary curvature deformity.
Figure 2:
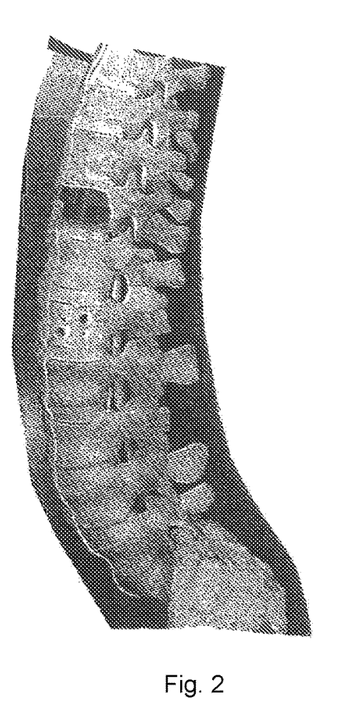
FIG. 2 illustrates a side view of a spine having a plate and screw affixed to a side vertebrae.
Figure 3:
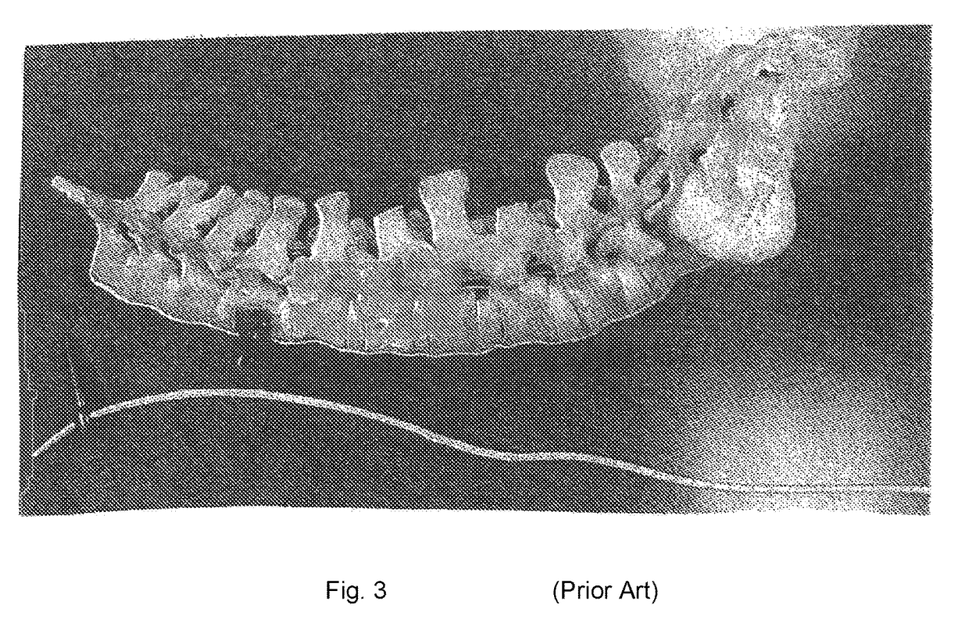

With regard to FIG. 1, the rear view of a spine having scoliosis is shown by way of background. FIG. 2 and FIG. 3 are illustrative of procedure affixing a plate/staple to a side of the anterior vertebrae of the spine. A screw configured through the plate has a head configured to receive a cord that can be tightened. Tightening of the cord provides compressive forces to one side of the spine while providing tensile forces to the opposite side during normal growth of the spine in juveniles.

Figure 4:
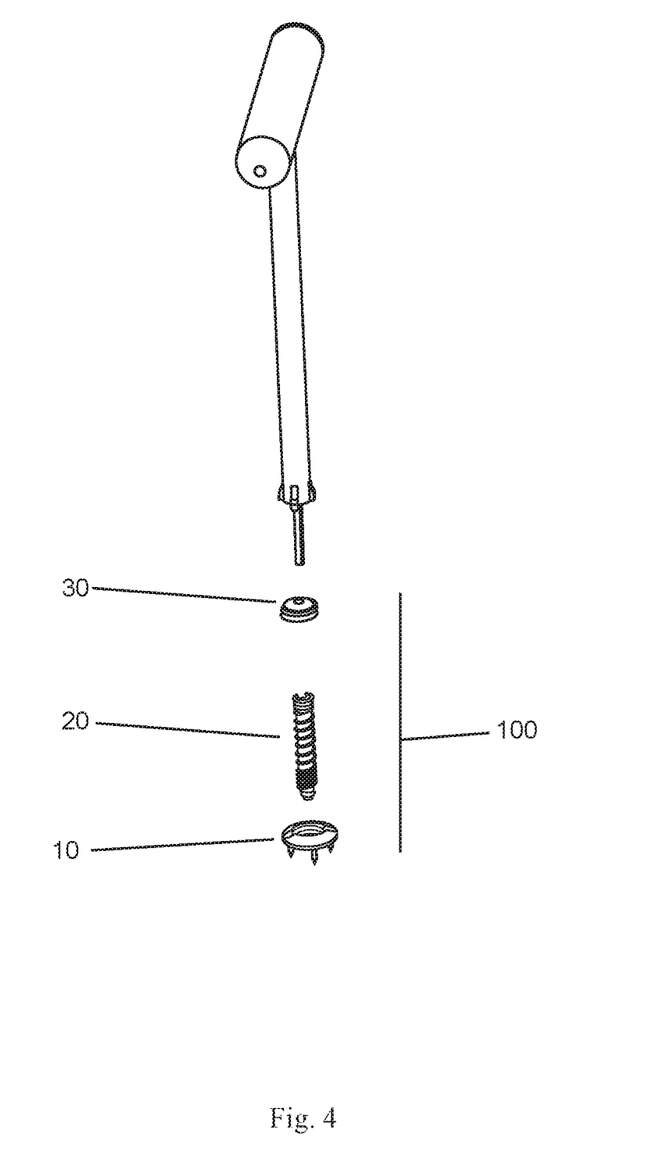
FIG. 4 illustrates an exploded view of the components of the present invention.

As can be seen in FIG. 3, the screw utilized in the prior art procedure in the posterior of the spine has a high profile which is uncomfortable when protruding from one side of the spine potentially aggravating the patient's lung and/or other surrounding tissues. The improved spine implant of the present invention is shown in FIG. 4. The bone implant 100 is further comprised of staple 10, bone screw 20 received through the staple, and locking screw 30 which when combined with a tether cord provides improvements to spine implants over the prior art. A plurality of bone implants 100 may be utilized along the length of the spine as necessary in order to facilitate correction of existing curvature.

Figure 5A:
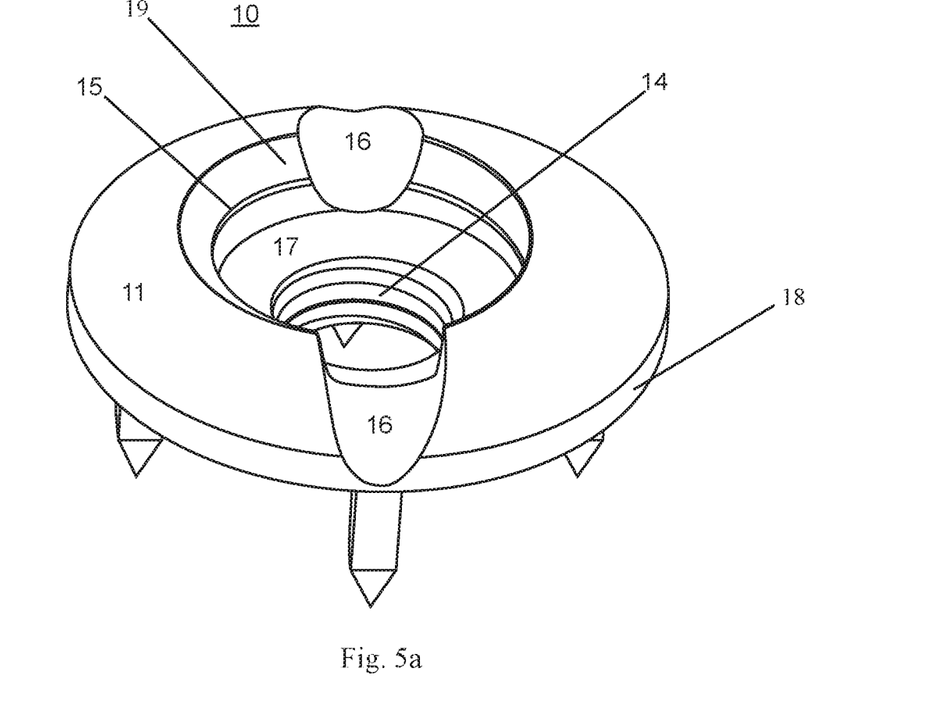
FIGS. 5(a) and (b) illustrate an exemplary threaded staple of the present invention; (a) shows a top perspective view and (b) shows a side perspective view.
Figure 5B:
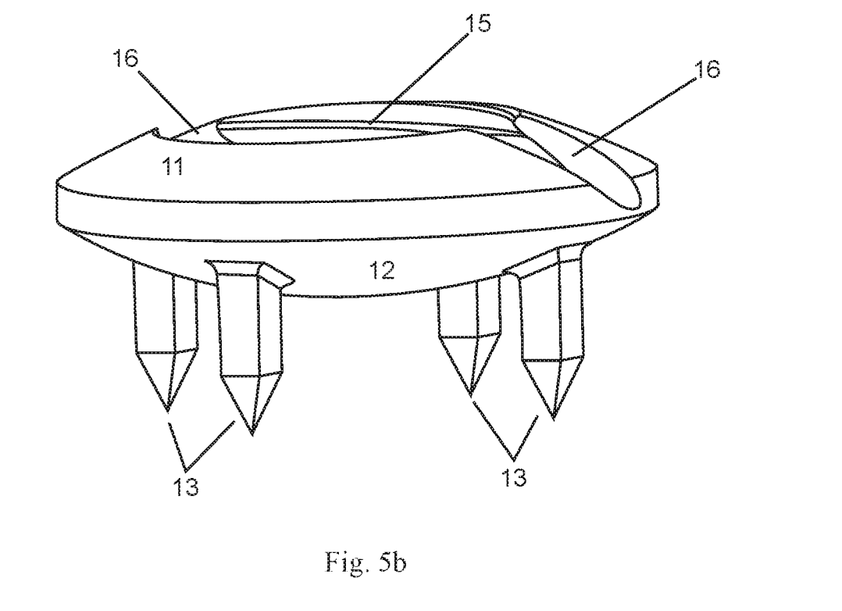

With regard to FIGS. 5a and 5b, staple 10 is shown in greater detail. In particular, staple 10 serves to facilitate locking of the tether cord (not shown) to bone implant 100 as well as disperse forces along the vertebral bone to which it is attached. In an exemplary embodiment, staple 10 is comprised of a domed upper surface 11 and domed lower surface 12, lower surface 12 having a plurality of spikes 13 for penetrating the vertebral bone. Domed upper surface 11 extends smoothly from an outer periphery 18 to a central pocket 19. The domed shape of staple 10 serves to create smooth margins thereby eliminating any irritation of surrounding soft tissue and also more accurately matching the structural anatomy of the vertebral bone to which it is attached. Staple 10 may further include lower inner threads 14 within pocket 19 for engaging with a bone screw 20 (not shown) thereby locking the staple 10 and bone screw 20 (not shown) together. Lower inner threads 14 may also accommodate a tool for installing staple 10 to the vertebral bone surface. Staple 10 may further include upper inner threads 15 located within pocket 19 for engaging with the locking screw 30 (not shown) thereby locking staple 10 and locking screw 30 (not shown) together. Staple 10 may also include an inner flat surface 17 to which locking screw 30 (not shown) will abut when secured and lock the tether cord within the implant. Domed upper surface 11 may have a cut-out 16 for accommodation of the tether cord. In a preferred embodiment, the cut-out 16 extends downward to intersect with the inner flat surface 17. A special instrument may interact with a further feature around the circumference or any surface of staple 10 to facilitate tensioning of the tether cord and implant complex.

Figure 6A:
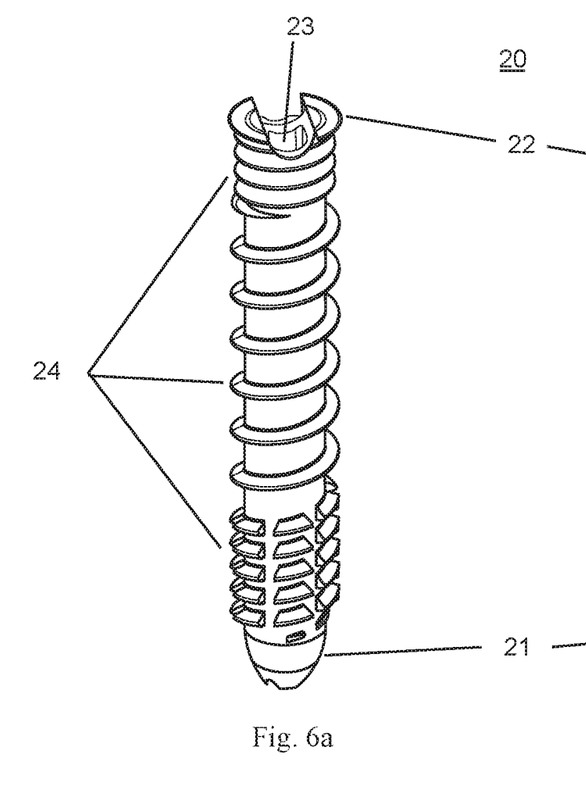
FIG. 6(a)-(d) illustrate an exemplary attachment screw of the present invention; (a) shows a side perspective view, (b) shows a side view, (c) shows a top perspective view and (d) shows a cross-section view.
Figure 6B:
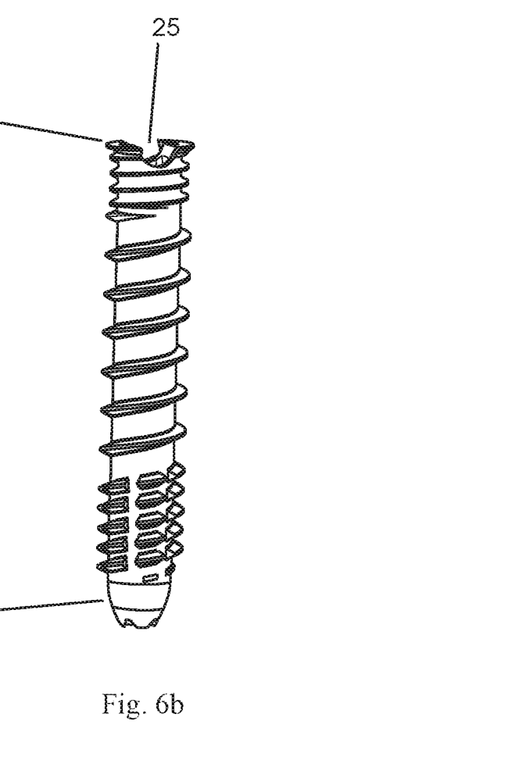
Figure 6C:
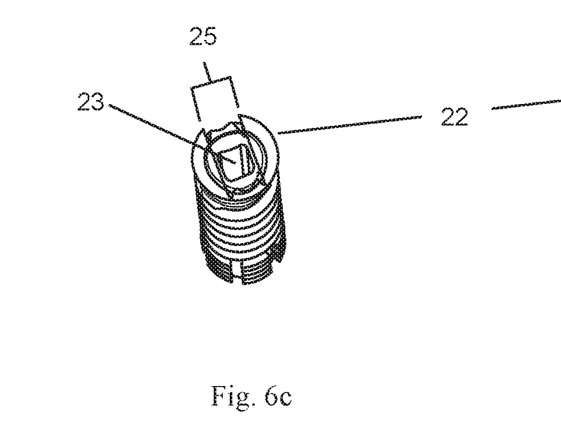
Figure 6D:
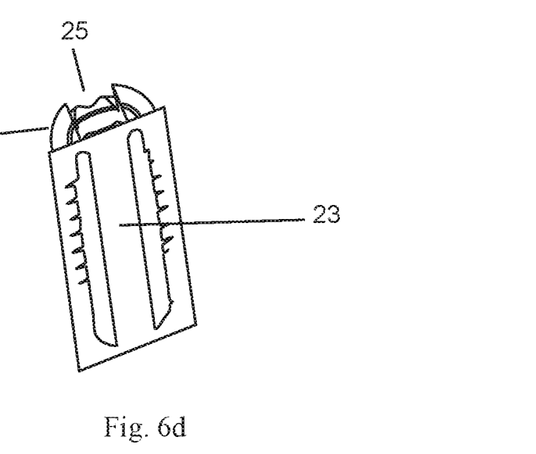

With regard to FIG. 6a-d, bone screw 20 is shown in greater detail. In particular, bone screw 20 secures staple 10 to the vertebral bone thereby locking staple 10 into place. In an exemplary embodiment, bone screw 20 is comprised of a tapered first end 21 and a flattened second end 22, as illustrated in FIGS. 6a and 6b. Flattened second end 22 may further include a tool feature 23 for instrument engagement. Flattened second end 22 may also include a cut-out 25 to accommodate at tightening instrument. Threads 24 of bone screw 20 may have separate and/or varying patterns or pitches alone the length of hone screw 20, including but not limited to, a combination of cancellous and cortical thread patterns or pitches to maximize attachment to the vertebral bone. Bone screw 20 may further include differing or varying diameters along its length. FIG. 6c shows a clear view of tool feature 23 and FIG. 6d illustrates tool feature 23 extending through the entire length of the bone screw 20.

Figures 7A, 7B:
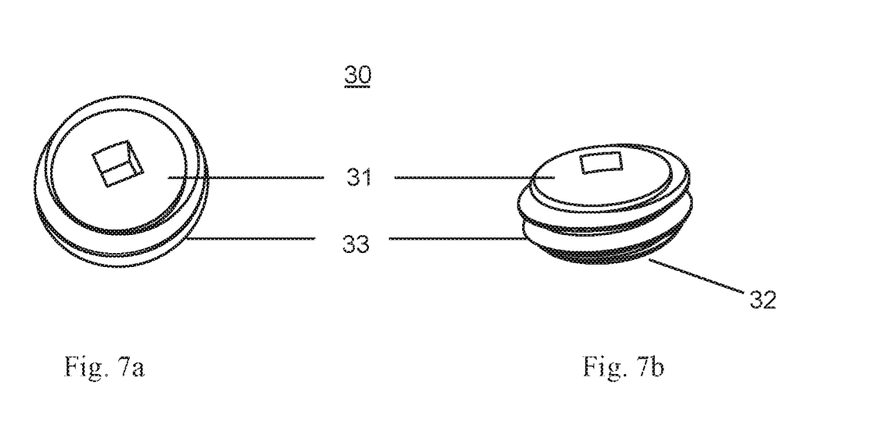
FIG. 7(a)-(c) illustrate an exemplary set screw of the present invention; (a) shows a top perspective view, (b) shows a side perspective view and (c) shows a side view.
Figure 7C:
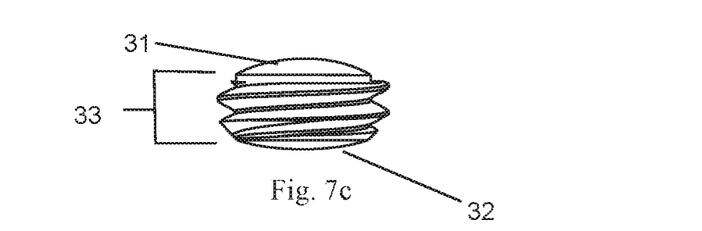

With regard to FIG. 7a-c, locking screw 30 is shown in greater detail. In particular, locking screw 30 serves to lock or secure the tether cord component between staple 10 and locking screw 30. In an exemplary embodiment, locking screw 30 is comprised of domed upper surface 31 and domed lower surface 32, whereby domed upper surface 31 creates a smooth margin so as to not irritate soft tissue surround the spine and domed lower surface 32 creates a locking force against the tether cord without causing damage. The length of locking screw 30 further includes threads 33 which lock the locking screw 30 into staple 10 of the implant system. Domed upper surface 31 further includes a tool feature 34 in the center, or other location(s), for a screwdriver instrument to engage. Alternatively, locking screw 30 may have protrusion on domed lower surface 32 to assist in securing the tether cord.

The tether cord component of the implant system is positioned between and adjacent to staple 10 and bone screw 20 within the cut-out 16 of staple 10 and connects adjacent implant systems attached to adjacent vertebrae. The tether cord allows for tensioning of adjacent implant systems. The tether cord may be flat, round, oblong, elliptical or any other shape desired and may be composed of a synthetic, natural or biologic material.

Figure 8:
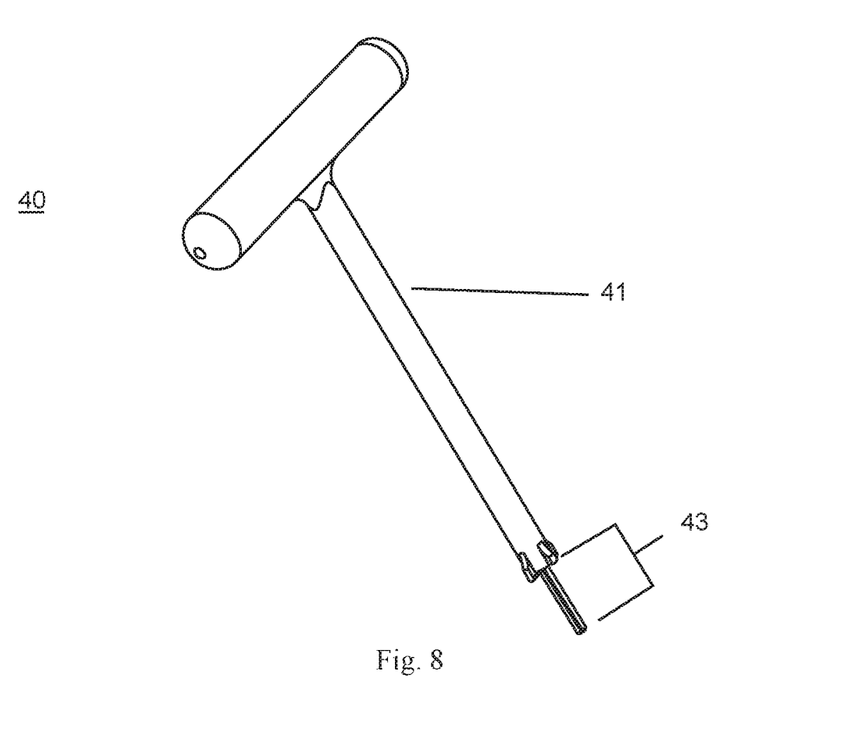
FIG. 8 illustrates a side perspective view of the screwdriver tool of the present invention.

With regard to FIG. 8, an exemplary screwdriver tool 40 is illustrated. Screwdriver tool 40 is comprised of a neck 41 having a handle 42 at the first end and a tool instrument 43 at the second end. Tool instrument 43 corresponds in shape to the tool features of staple 10, hone screw 20 and locking screw 30.

Figure 9A:
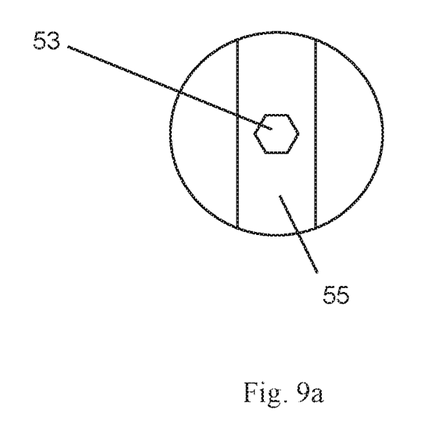
FIG. 9(a)-(c) illustrates an exemplary staple/screw combination of the present invention; (a) shows a top view, (b) shows a side view of a first embodiment and (c) shows a side view of an alternative embodiment.
Figure 9B:
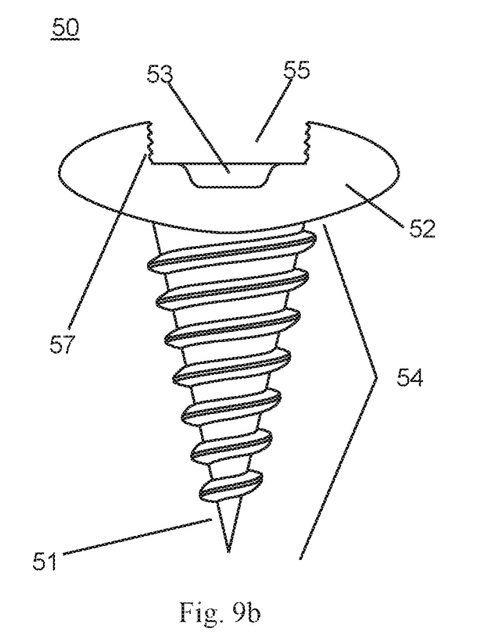
Figure 9C:
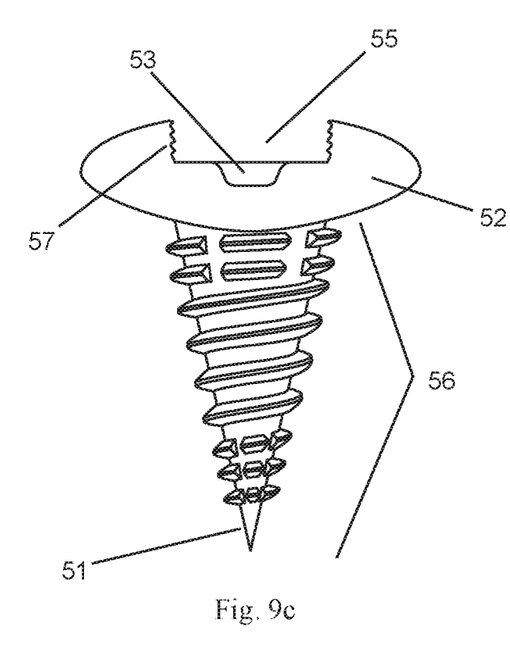

With regard to FIG. 9a-c an exemplary staple/bone screw 50 in a single unit is illustrated. In particular, the staple/bone screw 50 may or may not have a plurality of spikes for fixation of the staple/bone screw to bone and dispersal of forces. The staple/bone screw 50 is comprised of a tapered first end 51 resembling bone screw 20 (not shown) and a domed top end 52 resembling a staple 10 (not shown). The domed top end 52 of staple/bone screw 50 is further comprised of cut-out 55 to accommodate a tether cord, tool feature 53 and inner threads 57 for locking of the locking screw (not shown). The length of staple/bone screw 50 includes uniform threads 54 or varied threads 56.

While the particular invention as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

I claim:

1. A bone implant for treatment of skeletal abnormalities in an individual, the bone implant comprised of:
   a staple having an outer periphery and a central pocket and a smooth domed upper surface extending from the outer periphery to the central pocket, the central pocket including threads;
   a bone screw receivable through the central pocket; and
   a locking screw having threads adapted and configured for coupling to the threads of the pocket;
   wherein the smooth domed upper surface of the staple includes two cut outs each extending on the upper surface from the outer periphery to the central pocket, the cut outs being adapted and configured to accommodate therein the placement of a tether cord;
   wherein said locking screw has a bottom surface, and the two cut outs align a tether pathway that extends under the bottom surface of said locking screw.

2. The bone implant of claim 1 wherein the staple includes a domed lower surface, the domed upper surface and domed lower surface having rounded edges for reduction of irritation of soft tissue surrounding the implant.

3. The bone implant of claim 2, wherein the staple further includes a plurality of spikes protruding from the domed lower surface such that the spikes facilitate stable attachment to and dispersion of forces on the bone associated with the implant.

4. The bone implant of claim 1, wherein the bone screw is comprised of a first tapered end and second flat end, the first tapered end and the second flat end defining the length of the bone screw therebetween.

5. The bone implant of claim 1, wherein the bone screw includes threads disposed along the outer circumference of the length of said bone screw, the threads being of varying patterns or pitches.

6. The bone implant of claim 4, wherein the pocket of the staple has at least an inner, lower set of threads corresponding to the threads adjacent to the second flat end of the bone screw such that the staple and bone screw lock together once tightened into place within the associated bone.

7. The bone implant of claim 1, there the staple and the bone screw are integrated in a single unit, the single unit having a first tapered end and a second flat end.

8. The bone implant of claim 1, wherein the locking screw is comprised of a domed upper surface and a domed lower surface.

9. The bone implant of claim 1, wherein the complete inserted implant creates a smooth margin.

10. The bone implant of claim 1, wherein said staple includes a lower surface having a plurality of spikes extending therefrom, the spikes being adapted and configured to facilitate stable attachment to and dispersion of forces on the bone associated with the implant.

11. The bone implant of claim 1, wherein the two cut outs each extend on opposite sides of the central pocket and to the periphery, each cut out aligning with the other cut out.

* * * * *